United States Patent [19]
Strelow et al.

[11] Patent Number: 6,114,261
[45] Date of Patent: Sep. 5, 2000

[54] NONWOVEN ABSORBENT ARTICLE CONTAINING AN EMOLLIENT RESISTANT POLYBUTYLENE-BASED HOT MELT ADHESIVE

[75] Inventors: Diane M. Strelow, Waukesha; Margaret M. Oteman, Milwaukee; Mark A. Gibes, Port Washington, all of Wis.; Johannes Cornelis Maria Simons, Rilland, Netherlands; Mark D. Alper, Mukwonago, Wis.; Bonnie M. Harris, Wales, Wis.; Monina D. Kanderski, Milwaukee, Wis.

[73] Assignee: Ato Findley, Inc., Wauwatosa, Wis.

[21] Appl. No.: 09/238,119

[22] Filed: Jan. 27, 1999

Related U.S. Application Data

[63] Continuation-in-part of application No. 08/632,117, Apr. 15, 1996, Pat. No. 6,008,148.

[51] Int. Cl.[7] ....................................................... B32B 9/04
[52] U.S. Cl. .......................... 442/153; 442/381; 428/483; 428/507; 428/509; 428/512; 428/516
[58] Field of Search ..................................... 428/483, 507, 428/509, 512, 516; 442/381, 153

[56] References Cited

U.S. PATENT DOCUMENTS

| | | | |
|---|---|---|---|
| 4,568,713 | 2/1986 | Hansen et al. | 524/291 |
| 4,826,909 | 5/1989 | Lakshmanan et al. | 524/478 |
| 4,833,192 | 5/1989 | Lakshmanan et al. | 524/476 |
| 4,937,138 | 6/1990 | Mostert | 428/286 |
| 4,956,207 | 9/1990 | Kauffman et al. | 428/35.7 |
| 5,021,257 | 6/1991 | Foster et al. | 427/2 |
| 5,024,888 | 6/1991 | Hwo et al. | 428/355 |
| 5,041,492 | 8/1991 | Koprowicz et al. | 524/274 |
| 5,106,447 | 4/1992 | Di Rado et al. | 156/334 |
| 5,254,612 | 10/1993 | Sugi et al. | 524/274 |
| 5,455,111 | 10/1995 | Velasquez Urey | 428/315.5 |
| 5,786,418 | 7/1998 | Strelow et al. | 524/579 |

FOREIGN PATENT DOCUMENTS

| | | |
|---|---|---|
| 0331410 | 9/1989 | European Pat. Off. |
| WO90/00065 | 1/1990 | WIPO |
| WO92/12212 | 7/1992 | WIPO |

*Primary Examiner*—Helen L. Pezzuto
*Attorney, Agent, or Firm*—Andrus, Sceales, Starke & Sawall

[57] ABSTRACT

A polybutylene-based hot melt adhesive composition having a variety of end uses, particularly in construction and elastic attachment applications on nonwoven disposable articles. Unlike typical hot melt adhesives, the present composition can withstand exposure to emollients such as mineral oil and other oil-based ointments without experiencing catastrophic bond failure. The composition includes a polybutylene-based polymer or a mixture of a polybutylene-based polymer and a polyalphaolefin polymer, a tackifier resin, a plasticizer, a wax and a stabilizer. The hot melt adhesive composition can be applied using common application techniques such as extruding or spraying.

10 Claims, 3 Drawing Sheets

6,114,261

NONWOVEN ABSORBENT ARTICLE CONTAINING AN EMOLLIENT RESISTANT POLYBUTYLENE-BASED HOT MELT ADHESIVE

CROSS-REFERENCE TO RELATED APPLICATIONS

This application is a continuation-in-part of application Ser. No. 08/632,117 filed Apr. 15, 1996, now U.S. Pat. No. 6,008,148.

FIELD OF THE INVENTION

The present invention relates to hot melt adhesive compositions, and more particularly to an emollient resistant polybutylene-based hot melt adhesive which finds utility in construction and elastic attachment applications in nonwoven disposable absorbent articles such as diapers.

BACKGROUND OF THE INVENTION

Numerous types of nonwoven disposable absorbent articles are commercially available, and are manufactured for use in the absorption and containment of bodily waste such as urine and feces. Typical of such articles are disposable diapers for infants, and undergarments for incontinent adults. In the construction of such disposable articles, an inner leg gather or cuff is employed to prevent leakage of the bodily waste around the user's legs. During use, this cuff or flap is held in place with one or more elastic bands surrounding the leg. These elastic bands are typically held in place and attached to the disposable article by a hot melt adhesive.

While a wide range of hot melt adhesive compositions are known and used in the construction of disposable articles, it is also well known that a hot melt adhesive used for bonding in a particular use or application may be completely unsuitable for other uses or applications. Thus, various hot melt adhesive compositions are used in the construction of disposable articles. For example, it is well known that polyolefin-based hot melt adhesives are suitable for the construction of diapers, particularly in the bonding of polyethylene films, or the like, to issue or nonwoven substrates in the production of such articles. However, it is also known that most polyolefin-based hot melt adhesives are not suitable for bonding of the elastic bands in the diapers because their creep resistance is insufficient for such an application. For this reason, hot melt adhesives such as styrene-isoprene-styrene (SIS) block copolymers or styrene-butadiene-styrene (SBS) block copolymers are used.

These block copolymers, however, lose most of their bond strength upon exposure to oil-based emollients. Mineral oil and other oil-based ointments or lotions, referred to herein as emollients, are often rubbed on the skin of infants by the caregiver to treat and/or prevent skin rashes. Emollients may also be applied to or pre-coated on the non-woven skin-contacting layer of diapers and other absorbent articles by the manufacturers of such articles. It is believed that emollients disturb the bond of adhesives by two mechanisms. First, they migrate into the adhesive-substrate interface and thereby disrupt the bond. Second, the emollient is absorbed into and plasticizes the adhesive which reduces the cohesive strength of the adhesive. Thus, prior hot melt adhesive compositions, upon exposure thereto, experience adhesive bond failure. As a result, the elastic leg bands may actually let loose from the diaper resulting in complete failure and break down of the inner leg cuff. Also, construction adhesives may fail resulting in undesirable delamination of the absorbent article. Therefore, an adhesive that is capable of withstanding exposure to emollients while still providing sufficient bond strength would be highly desirable.

SUMMARY OF THE INVENTION

The present invention is directed to a laminate structure for use in a disposable absorbent article, preferably a diaper. The laminate structure includes a substrate, a topsheet having a first surface facing the substrate and a second skin-engaging surface, and an emollient resistant hot melt adhesive disposed between and bonding the substrate to the topsheet. The hot melt adhesive used in the laminate of the present invention maintains acceptable bond strength even after exposure to an emollient.

The substrate and/or the topsheet may each independently be a layer of absorbent cellulosic material, absorbent fluff, superabsorbent polymers, elastic material, nonwoven fabric, tissue, a polyolefin, a polyester or combinations thereof. Any layer typically used in disposable absorbent articles, such as diapers, may comprise the substrate and/or topsheet used in the laminate of the present invention.

An emollient is present in the laminate either as a pre-applied coating on the skin-engaging surface of the topsheet, or upon contact of the topsheet with another surface, such as skin, coated therewith. In the former situation, the emollient may be pre-applied by a manufacturer of disposable absorbent articles. In the latter situation, a caregiver or user has typically applied or coated the skin with the emollient which thereafter contacts the topsheet.

The emollient resistant hot melt adhesive composition used in the laminate of this invention can be particularly useful in disposable nonwoven articles such as diapers to resist the de-bonding action that would otherwise occur when an emollient contacts a conventional hot melt adhesive. These hot melt adhesive compositions can provide good elastic attachment bonds when tested via standard creep resistance test methods, and can also provide excellent bonds when tested via standard peel strength tests both before and after exposure to an emollient. In addition, the hot melt adhesive maintains excellent dry bond strength even after exposure to elevated temperature aging, i.e. simulated warehouse conditions.

The adhesive of the present invention can be used in any of a number of applications within the disposable article itself. For example, the adhesive can be formulated for use in bonding a topsheet to a tissue, nonwoven, distribution layer, or to absorbent fluff/superabsorbent material. In this application, the adhesive will provide a bond that is not destroyed by emollient coated onto the topsheet. This is surprising given that the emollients are chemically compatible with the compositions of the adhesive used in the laminate of the present invention.

In addition, the adhesive can also be formulated to bond cellulosic materials where "high wet-strength" bonds are required. Traditional hot melt adhesives which have been formulated using SIS, SBS, SEBS and APAO have a propensity when exposed to water for prolonged periods of time, to lose their bond strengths, with the result that laminations prepared with such adhesives will fail when exposed for prolonged periods of time to water. Such delaminations of a nonwoven garment, such as a diaper or the like may cause the garment's core integrity to fail with resulting undesirable effects such as leaking or poor fit. The adhesive of the present invention, however, resists delamination caused by exposure to moisture.

Finally, the adhesive can also be formulated for elastic attachment applications. That is, for bonding elastic strands, films, or foams between other substrates (such as nonwovens). These bonds are under stress during use and the bond must be maintained in the presence of emollients.

The hot melt adhesive composition of the present invention comprises a blend of the following:

(a) about 10% to 65% by weight of a polybutylene copolymer, homopolymer, or blend thereof;

(b) about 0% to 65% by weight of a polyalphaolefin copolymer;

(c) about 15% to about 70% by weight of a tackifying resin;

(d) about 0% to about 30% by weight of a plasticizer;

(e) about 0% to about 20% by weight of a wax; and (f) about 0.1% to about 2% by weight of a stabilizer.

The minimum polymer content is preferably about 20% by weight.

A preferred hot melt adhesive composition (see Example 1) functioning exceptionally well as a construction and core adhesive while also providing adequate bond strength after emollient exposure comprises a blend of the following:

(a) about 40% by weight of a fully hydrogenated hydrocarbon tackifying resin;

(b) about 29% by weight of a liquid hydrocarbon tackifying resin;

(c) about 30% by weight of a polybutylene copolymer; and (d) about 1% by weight of an antioxidant stabilizer.

A preferred hot melt adhesive composition (see Example 2) functioning exceptionally well as an elastic attachment adhesive while providing adequate bond strength after emollient exposure comprises a blend of the following:

(a) about 51% by weight of a fully hydrogenated hydrocarbon tackifying resin;

(b) about 30% by weight of a polybutylene copolymer;

(c) about 7% by weight of a polybutylene homopolymer;

(d) about 11% by weight of a wax; and (e) about 1% by weight of an antioxidant stabilizer.

The following adhesive composition (see Example 3) performed exceptionally well as an elastic attachment adhesive while also providing adequate creep performance after emollient exposure:

(a) about 18% by weight of a fully hydrogenated hydrocarbon tackifying resin;

(b) about 5% by weight of a liquid hydrocarbon tackifying resin;

(c) about 19% by weight of a polybutylene copolymer;

(d) about 19% by weight of a polybutylene homopolymer;

(e) about 28% by weight of a polyalphaolefin copolymer;

(f) about 10% by weight of a wax; and (g) about 1% by weight of an antioxidant stabilizer.

The hot melt adhesive compositions used in the laminates of the present invention thus possess, depending upon the particular formulation, sufficient creep resistance to perform as an elastic attachment adhesive in a nonwoven disposable article, sufficient bond strength to perform as a construction or high wet strength core adhesive in a nonwoven disposable absorbent article, good peel adhesion to polyolefin films after elevated temperature aging, and exhibit acceptable bond strength after emollient exposure.

DETAILED DESCRIPTION OF THE INVENTION

As used herein, the term "diaper" refers to an absorbent article typically worn by infants, young children and incontinent adult persons. As readily understood, such an absorbent article is worn about the lower torso of the wearer and is held in place about the wearer's hips. It should be understood, however, that the present invention is also applicable to other absorbent articles such as training pants, incontinent products such as briefs and undergarments, feminine care products such as sanitary napkins and pantyliners, medical products, such as surgical drapes and the like.

As used herein, the term "absorbent article" refers to a device or product which absorbs and contains body fluids and exudates such as urine. More specifically, this term refers to such devices or articles that are worn against or in proximity to the body of a wearer to absorb and contain various fluids and exudates discharged from the body. The term "disposable" is used herein to describe absorbent articles which are to be discarded after a single use. Such articles are not intended to be laundered or otherwise re-used as an absorbent article. Preferred embodiments of absorbent articles of the present invention are diaper 10 schematically shown in FIGS. 1 and 2 and feminine care pad 11 schematically illustrated in FIG. 3.

Figure 1:
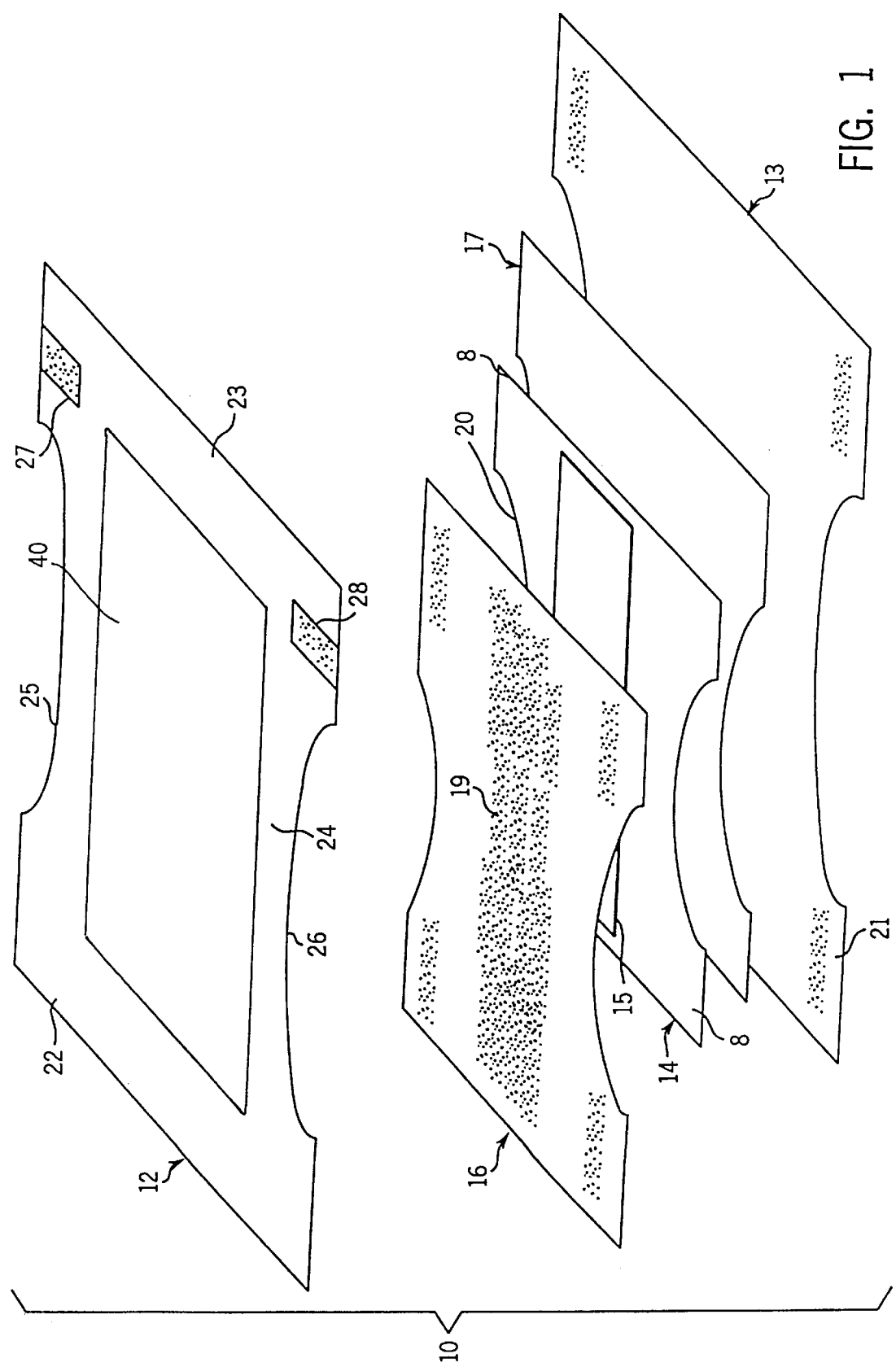
FIG. 1 is a schematic exploded, perspective view of a disposable diaper having a laminate structure incorporating an emollient resistant hot melt adhesive constructed in accordance with the present invention.
Figure 2:
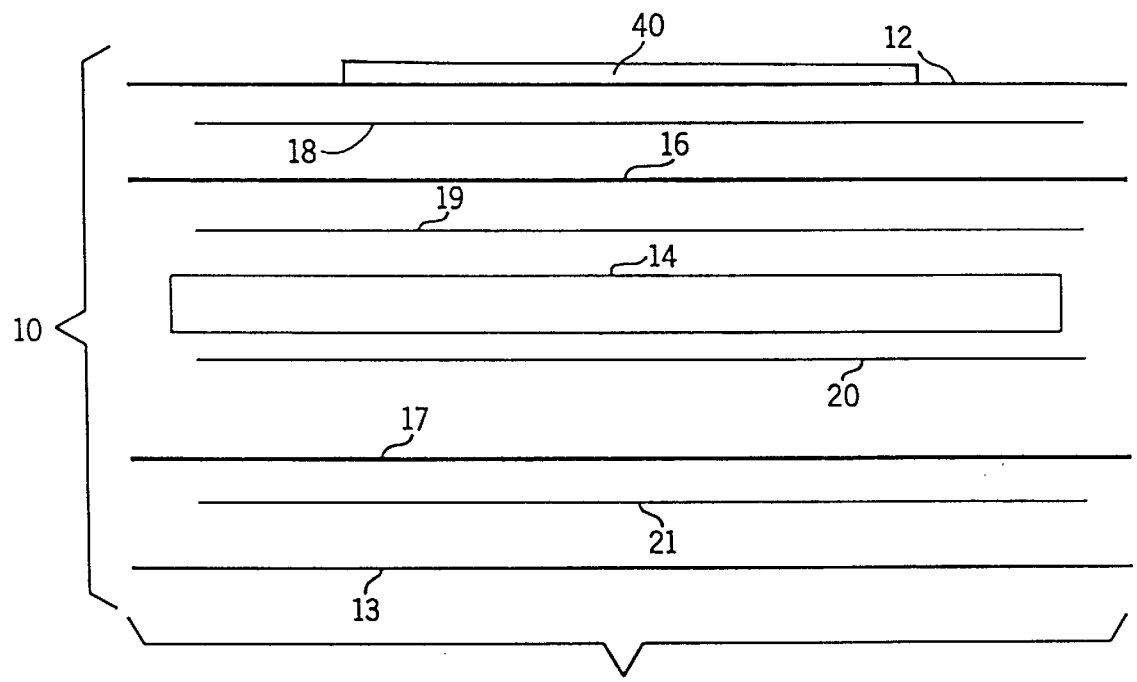
FIG. 2 is a schematic cross-sectional view of the diaper of FIG. 1.

Referring now to FIGS. 1 and 2 there is illustrated in FIG. 1 an exploded view of various substrates comprising diaper 10 in its flat, uncontracted state with portions of the structure being shown schematically to more clearly show the construction of diaper 10. FIG. 2 schematically illustrates in cross section the multiple layers or substrates of diaper 10.

As shown, diaper 10 comprises multiple layers of sheet material or substrates adhesively bonded together to form the absorbent article. More specifically, diaper 10 includes a fluid pervious nonwoven topsheet 12 and a fluid impervious backsheet 13 (typically composed of a polyolefin material such as polyethylene or polypropylene) joined with topsheet 12. An absorbent core 14 is positioned between topsheet 12 and backsheet 13. Absorbent core 14 may be comprised of fluff 8 and, optionally, a centrally disposed superabsorbent polymer (SAP) material 15. Fluff 8 is typically composed of absorbent fibers such as cellulose fibers, but may also include other absorbent natural or synthetic fibers and/or materials.

As noted above, the absorbent core 14 may contain discrete particles of a superabsorbent material 15. Superabsorbents are those materials which, upon contact with liquids such as water and body fluids, imbibe and retain such liquids and thereby form hydrogels. In this manner, liquids discharged into the absorbent core 14 can be acquired and held by the particles, thereby providing enhanced absorbent capacity and/or improved liquid retention performance.

Diaper 10 may also include a top tissue layer 16 disposed between topsheet 12 and core 14 as well as a bottom tissue layer 17 disposed between backsheet 13 and core 14. As shown best in FIG. 2, each substrate can be bonded to an adjacent substrate by a layer of emollient resistant adhesive formulated in accordance with the present invention. For example, nonwoven topsheet 12 is bonded to top tissue layer 16 by a layer of adhesive 18 applied to the underside of topsheet 12. In turn, top tissue layer 16 is bonded to core 14 by a layer of adhesive 19. Core 14 is bonded to bottom tissue layer 17 by a layer of adhesive 20 and bottom tissue layer 17 in turn is bonded to a backsheet 13 by a layer of adhesive 21 applied to the upper surface of backsheet 13. The adhesive may be sprayed, spiral sprayed, melt blown, slot applied or may be applied as a bead depending upon the location and the type of bond desired.

As shown best in FIG. 1, diaper 10 includes a pair of opposite waist panels 22, 23 interconnecting a crotch portion 24. Crotch portion 24 in turn includes a pair of opposite elasticized leg cuffs 25, 26. The waist panels 22, 23 are held together when diaper 10 is worn by a user by a fastening system which is illustrated in FIG. 1 as a pair of releasable tape tabs 27, 28.

Figure 3:
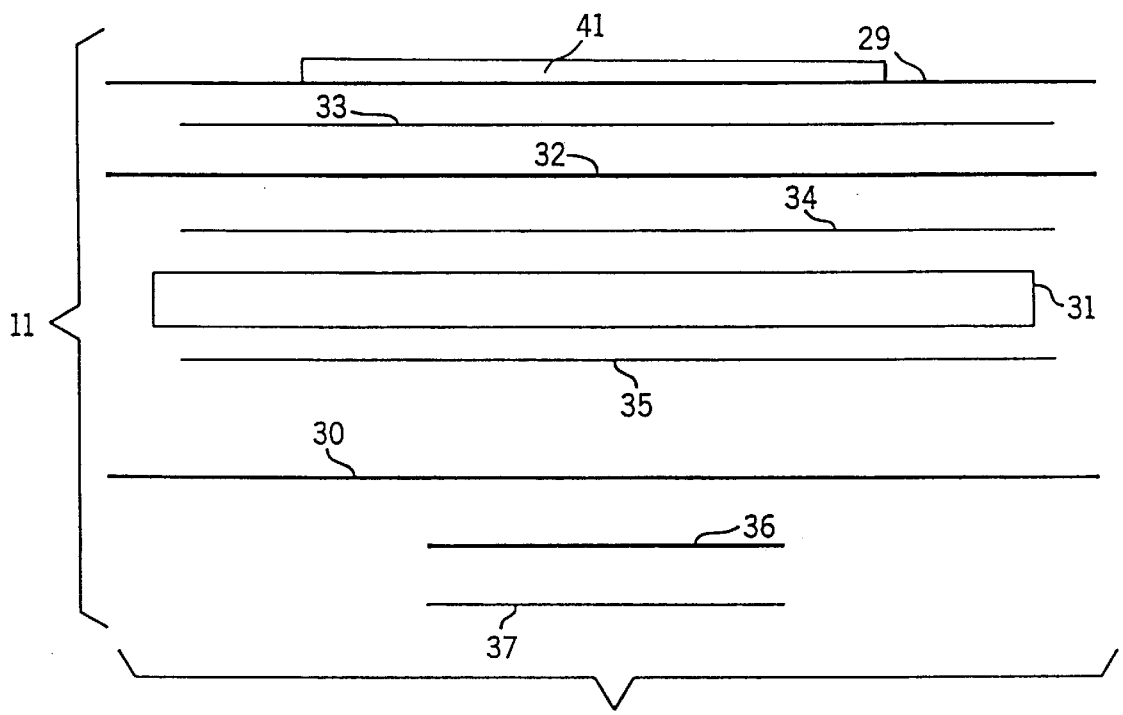
FIG. 3 is a schematic cross-sectional view of a disposable feminine care pad having a laminate structure incorporating an emollient resistant hot melt adhesive constructed in accordance with the present invention.

Referring now to FIG. 3, there is illustrated an absorbent article illustrating a typical feminine care pad 11. Pad 11 comprises multiple layers of sheet material or substrates bonded together to form the absorbent article. More particularly, pad 11 includes a fluid pervious nonwoven topsheet 29 and a fluid impervious backsheet 30 (typically composed of a polyolefin material such as polyethylene or polypropylene) joined with topsheet 29. An absorbent core 31 is positioned between topsheet 29 and backsheet 30. Absorbent core 31 may be comprised of fluff and/or super absorbent (SAP) material. Pad 11 may also include a top tissue layer 32 disposed between top sheet 29 and core 31. As shown in FIG. 3, each substrate can be bonded to an adjacent substrate by a layer of adhesive formulated to be emollient resistant in accordance with the present invention. For example, nonwoven topsheet 29 is bonded to top tissue layer 32 by a layer of adhesive 33 applied to the underside of top sheet 29. In turn, top tissue layer 32 is bonded to core 31 by a layer of adhesive 34. Finally, core 31 is bonded to backsheet 30 by a layer of adhesive 35 applied to the upper surface of backsheet 30. In addition, the absorbent fibers of core 31 themselves may be bonded together to form a cohesive, self-supporting absorbent core, as will hereinafter be explained. The adhesive may be sprayed, spiral sprayed, melt blown, slot applied or may be applied as a bead depending upon the location and the type of bond desired. In the embodiment illustrated in FIG. 3, there is also a layer of a conventional pressure sensitive pad attachment adhesive 36 applied to the bottom side of backsheet 30 and release paper 37 covering adhesive 36. Thus, when paper 37 is removed to expose adhesive 36, adhesive layer 36 may be utilized to attach pad 11 to an undergarment worn by the user, as is conventional and well known in the art.

Manufacturers of feminine care pads, diapers and other absorbent articles may from time to time apply a coating 40 of emollient on the skin-engaging surface of top sheet 12 of diaper 10 (FIG. 2) or a coating 41 of emollient on the skin-engaging surface of topsheet 29 of feminine care pad 11 (FIG. 3). This emollient is intended to help prevent skin rashes that may develop during use of absorbent articles. As used herein, the term "emollient" refers to saturated or unsaturated liquid hydrocarbons such as mineral oil, glycerin, petroleum jelly, petrolatum, aloe vera, low molecular weight polyethylene, polyethylene oxide, polypropylene oxide, polytetramethylene oxide, soft carbowax, microcrystalline waxes, petroleum waxes, atactic polypropylene, synthetic waxes, polyolefin waxes, plasticizing oils, and the like. The above emollients may be in liquid, solid or semi-solid form. Petrolatum is particularly preferred because of its relatively low cost and excellent properties. However, due to its effect on the bond strength of hot melt adhesives typically used in the past to bond together the laminate substrates of an absorbent article, a new oil-resistant adhesive has been developed and will hereinafter now be described.

A polybutylene-based hot melt adhesive composition having ingredients in the following ranges provides advantages over current technology when evaluated for retention of bond strength after emollient exposure. More particularly, the adhesive composition includes about 10% to 65% by weight of polybutylene, or a mixture of polybutylene and polyalphaolefin. Whether polybutylene is utilized alone or in a mixture of polybutylene and polyalphaolefin, the minimum polymer content in the composition should be about 20% by weight. Depending on end use and desired properties, the polyalphaolefin ingredient may be absent. Lack of the polyalphaolefin component is particularly acceptable when the adhesive composition is used in an elastic attachment application. The hot melt adhesive composition of the present invention also includes about 15% to about 70% tackifying resin, about 0% to about 30% by weight plasticizer, about 0% to about 20% by weight wax, and about 0.1% to about 2% by weight stabilizer.

The polybutylene copolymer, homopolymer, or blend thereof, component is used in the thermoplastic hot melt adhesive of the present invention to enhance the strength of the adhesive bond of the material at elevated temperatures, which is necessary for elastic attachment applications, and to provide oil resistance to the composition. As used herein, the term "polybutylene copolymer" refers to those polymeric entities comprised of ethylene and butene monomers where the butene monomeric unit comprises at least 89% of the copolymer. Polybutylene homopolymer can also be used as well as a copolymer and homopolymer blend. These are available from the Montell Co. under the trade name "Duraflex." A suitable commercially available butene-1-ethylene copolymer can be secured from Montell Company under the tradename Duraflex 8910 PC or Duraflex 8510. The preferred materials have a Ring and Ball softening point of approximately 150° C. (302° F.). Although a range of 10–65% by weight polybutylene copolymer, homopolymer, or blend thereof, may be used, the preferred range is 20% to 45%.

Butene-1-homopolymers and copolymers which are useful in the present invention are primarily linear chain molecules with regular and spatially ordered arrangements of ethyl side groups. These side groups are the result when butene-1 is polymerized across the 1, 2, carbon double bond, and along an ethylene chain backbone. This is described in further detail in U.S. Pat. No. 3,362,940. When cooled from a melt, the ethyl side groups initially align in a tetragonal spatial arrangement. With time the tetragonal crystalline phase form transfers into a stable hexagonal spatial arrangement with a subsequent development of improved physical properties. A more thorough discussion of the polymer utilized herein may be found in the reference to Mostert, U.S. Pat. No. 4,937,138, the contents of which is incorporated by reference herein. As will be seen from the disclosure above, the present polymer is useful in amounts of about 10% to about 65%, by weight.

The amorphous copolyolefin copolymer component, i.e. the polyalphaolefin copolymer, of the composition of the present invention is a copolymer-based on repeating units of ethylene, propylene, butene, or hexene. For example, they may be comprised of alternating repeating units of the following monomer combinations:

(a) Ethylene and propylene
(b) Ethylene and butene
(c) Propylene and butene
(d) Ethylene, propylene and butene Suitable copolymers are commercially available from Huntsman under the trade name "Rextac." It will be recognized that mixtures of any of the above copolymers also may be used as base components in the compositions of the present invention. The polyalphaolefin copolymer functions to provide adhesion to nonporous substrates. A range of 0–65% by weight polyalphaolefin copolymer may be used.

It should be noted that mixtures of the polybutylene copolymer, homopolymer, or blend thereof, and polyalphaolefin copolymer may also be used as long as a sufficient amount of polybutylene copolymer, homopolymer, or blend thereof, is employed to impart the desired amount of creep resistance to the adhesive composition. The minimum total polymer content in the composition should be about 20%. Thus, depending on the end use, and as noted above, the polyalphaolefin component could be absent from the composition.

The tackifying resins which are used in the hot melt adhesives of the present invention are those which extend the adhesive properties and improve the specific adhesion of the polybutylene copolymer, homopolymer, or blend thereof, and/or the polyalphaolefin copolymer. As used herein, the term "tackifying resin" includes:

(a) natural and modified rosin such as, for example, gum rosin, wood rosin, tall-oil rosin, distilled rosin, hydrogenated rosin, dimerized rosin and polymerized rosin;

(b) glycerol and pentaerythritol esters of natural and modified rosins, such as, for example, the glycerol ester of pale wood rosin, the glycerol ester of hydrogenated rosin, the glycerol ester of polymerized rosin, the pentaerythritol ester of pale wood rosin, the pentaerythritol ester of hydrogenated rosin, the pentaerythritol ester of tall oil rosin and the phenolic modified pentaerythritol ester of rosin;

(c) polyterpene resins having a softening point, as determined by ASTM method E28-58T, of from about 10° C. to 140° C., the latter polyterpene resins generally resulting from the polymerization of terpene hydrocarbons, such as the mono-terpene known as pinene, in the presence of Friedel-Crafts catalysts at moderately low temperatures; also included are the hydrogenated polyterpene resins;

(d) copolymers and terpolymers of natural terpenes, e.g. styrene/terpene, α-methyl styrene/terpene and vinyl toluene/terpene;

(e) phenolic-modified terpene resins such as, for example, the resin product resulting from the condensation, in an acidic medium, of a terpene and a phenol;

(f) aliphatic petroleum hydrocarbon resins having Ring and Ball softening points of from about 10° C. to 140° C., the latter resins resulting from the polymerization of monomers consisting primarily of olefins and diolefins; also included are the hydrogenated aliphatic petroleum hydrocarbon resins; examples of such commercially available resins based on a $C_5$-olefin fraction of this type are "Wingtack 95" and "Wingtack 115" tackifying resins sold by Goodyear Tire and Rubber Company;

(g) aromatic petroleum hydrocarbons and the hydrogenated derivatives thereof;

(h) aliphatic/aromatic petroleum derived hydrocarbons and the hydrogenated derivatives thereof.

Mixtures of two or more of the above described tackifying resins may be required for some formulations. Although a range of 15–70% by weight tackifying resin may be used, the preferred range is 20% to 50%. Tackifying resins which are useful for the present invention can perhaps include polar tackifying resins, however, the choice of available polar tackifying resins is limited in view of the fact that many of the polar resins appear only partially compatible with the butene-1-homopolymer, and copolymers.

As noted above, tackifying resins which are useful within the scope of the present invention comprise about 15% to about 70% by weight. Preferably, the tackifying resins can be selected from any of the nonpolar types, which are commercially available. Preferred resins are aliphatic petroleum hydrocarbon resins examples of which are based on a C5 olefin such as Wingtack 95 available from Goodyear Tire and Rubber Company. Most preferred are nonpolar tackifying resins which are completely hydrogenated $C_9$ or pure monomer-based hydrocarbon resins with softening points that are in a range of approximately 70° C. to approximately 125° C. An example of a commercially available tackifying resin which is most preferred in the present invention includes the resin which is identified commercially by the trade designation Regalrez 1094 available from Hercules.

A plasticizer can be present in the composition of the present invention in amounts of about 0% to about 30%, by weight, preferably from about 5% to about 15%, in order to provide desired viscosity control. A suitable plasticizer may be selected from the group which includes the usual plasticizing oils, such as mineral oil, but also olefin oligomers and low molecular weight polymers, as well as vegetable and animal oil and derivatives of such oils. The petroleum derived oils which may be employed are relatively high boiling temperature materials containing only a minor proportion of aromatic hydrocarbons. In this regard, the aromatic hydrocarbons should preferably be less than 30%, and more particularly less than 15%, by weight, of the oil. Preferably, the oil may be totally non-aromatic. The oligomers may be polypropylenes, polybutenes, hydrogenated polyisoprene, hydrogenated butadiene, or the like having average molecular weights between about 350 and about 10,000. Suitable vegetable and animals oils include glycerol esters of the usual fatty acids and polymerization products thereof. The plasticizer that finds usefulness in the present invention can be any number of different plasticizers but the inventors have discovered that a plasticizer which includes a mono-olefin polymer such as what is commercially available under the trade designation Indopol H-100, and which is manufactured by Amoco, is particularly useful in the present invention. Other liquid polybutenes having average molecular weights less than 5,000 may also be used. As will be appreciated, plasticizers have typically been employed to lower the viscosity of the overall adhesive composition without substantially decreasing the adhesive strength and/or the service temperature of the adhesive as well as extend the open time of the adhesive.

The waxes which can be used in amounts varying between 0% to 30% by weight, preferably 5% to 15%, in the composition of the present invention are used to reduce the melt viscosity of the hot melt construction adhesives without appreciably decreasing their adhesive bonding characteristics. These waxes also reduce the open time of the composition without effecting the temperature performance. Among the useful waxes are:

(1) low molecular weight, that is, 1000–6000, polyethylene having a hardness value, as determined by ASTM method D-1321, of from about 0.1 to 120 and ASTM softening points of from about 150° F. to 250° F.;

(2) petroleum waxes such as paraffin wax having a melting point of from about 130° F. to 175° F. and microcrystalline wax having a melting point of from about 135° F. to 200° F., the latter melting points being determined by ASTM method D 127-60;

(3) atactic polypropylene having a Ring and Ball softening point of from about 120° C. to 160° C;

(4) synthetic waxes made by polymerizing carbon monoxide and hydrogen such as Fischer-Tropsch wax; and (5) polyolefin waxes. As used herein, the term "polyolefin wax" refers to those polymeric or long-chain entities comprised of olefinic monomer units. These materials are commercially available from Eastman Chemical Co. under the trade name "Epolene." The materials which are preferred for use in the compositions of the present invention have a Ring and Ball softening point of 200° F. to 350° F. As should be understood, each of these wax diluents is solid at room temperature. Other useful substances include hydrogenated animal, fish and vegetable fats and oils such as hydrogenated tallow, lard, soya oil, cottonseed oil, castor oil, menhadin oil, cod liver oil, etc., and which are solid at ambient temperature by virtue of their being hydrogenated, have also been found to be useful with respect to functioning as a wax diluent equivalent. These hydrogenated materials are often referred to in the adhesives industry as "animal or vegetable waxes." Additionally, hydrocarbon oils, especially naphthenic or paraffinic process oils, may also be employed herein as the wax diluent.

The present invention includes a stabilizer in an amount of from about 0.1% to about 2% by weight, but preferably from about 0.1% to 1%. The stabilizers which are useful in the hot melt adhesive compositions of the present invention are incorporated to help protect the polymers noted above, and thereby the total adhesive system, from the effects of thermal and oxidative degradation which normally occurs during the manufacture and application of the adhesive as well as in the ordinary exposure of the final product to the ambient environment. Such degradation is usually manifested by a deterioration in the appearance, physical properties and performance characteristics of the adhesive. Among the applicable stabilizers are high molecular weight hindered phenols and multifunctional phenols, such as sulfur and phosphorous-containing phenols. Hindered phenols are well known to those skilled in the art and may be characterized as phenolic compounds which also contain sterically bulky radicals in close proximity to the phenolic hydroxyl group thereof. In particular, tertiary butyl groups generally are substituted onto the benzene ring in at least one of the ortho positions relative to the phenolic hydroxyl group. The presence of these sterically bulky substituted radicals in the vicinity of the hydroxyl group serves to retard its stretching frequency and correspondingly, its reactivity; this steric hindrance thus providing the phenolic compound with its stabilizing properties. Representative hindered phenols include:

1,3,5,-trimethyl-2,4,6-tris(3-5-di-tert-butyl-4-hydroxybenzyl) benzene;

pentaerythritol tetrakis-3(3,5-di-tert-butyl-4-hydroxyphenyl) propionate;

n-octadecyl-3(3,5-di-tert-butyl-4-hydroxyphenyl) propionate;

4,4'-methylenebis(4-methyl-6-tert butylphenol);

4,4'-thiobis(6-tert-butyl-o-cresol);

2,6-di-tert-butylphenol;

6-(4-hydroxyphenoxy)-2,4-bis(n-ocytlthio)-1,3,5-triazine;

2,4,6-tris(4-hydroxy-3,5-di-tert-butyl-phenoxy)-1,3,5-triazine;

di-n-octadecyl-3,5-di-tert-butyl-4-hydroxybenzylphosphonate;

2-(n-octylthio)ethyl-3,5-di-tert-butyl-4-hydroxybenzoate; and sorbitol hexa-(3,3,5-di-tert-butyl-4-hydroxy-phenyl) propionate.

Especially preferred as a stabilizer is pentaerythritol tetrakis-3(3,5-di-tert-butyl-4-hydroxyphenol) propionate.

The performance of these stabilizers may be further enhanced by utilizing, in conjunction therewith; (1) synergists such as, for example, as thiodipropionate esters and phosphites; and (2) chelating agents and metal deactivators as, for example, ethylenediaminetetraacetic acid, salts thereof, and disalicylalpropylenediimine.

The hot melt adhesive composition of the present invention may be formulated using any of the techniques known in the art. A representative example of the prior art procedure involves placing all of the substances, in a jacketed mixing kettle, and preferably in a jacketed heavy duty mixer of the Baker-Perkins or Day type, and which is equipped with rotors, and thereafter raising the temperature of this mixture to a range of about 250° F. to 350° F. It should be understood that the precise temperature to be used in this step would depend on the melting point of the particular ingredients. The resulting adhesive composition is agitated until the polymers completely dissolve. A vacuum is then applied to remove any entrapped air.

It should be understood that other optional additives may be incorporated into the adhesive composition of the present invention in order to modify particular physical properties. These may include, for example, such materials as colorants, fillers, fluorescent agents, surfactants, etc.

The invention is further illustrated by way of the examples which are set forth below.

EXAMPLE 1

The following adhesive blend was prepared in accordance with the present invention. When tested, the adhesive performed exceptionally well as a construction and core adhesive while also providing adequate bond strength after emollient exposure.

| Weight % | Ingredient | Commercial Source | Generic Name |
|---|---|---|---|
| 40 | Regalrez 1094 | Hercules | Resin |
| 29 | Excorez 2520 | Exxon | Resin |
| 30 | Polybutylene 8510 | Montell | Polybutylene |
| 1 | Irganox 1010 | Ciba Additives | Stabilizer |

EXAMPLE 2

The following adhesive blend was prepared in accordance with the present invention. When tested, the adhesive performed exceptionally well as an elastic attachment while also providing adequate creep performance after emollient exposure.

| Weight % | Ingredient | Commercial Source | Generic Name |
|---|---|---|---|
| 51 | Regalrez 1094 | Hercules | Resin |
| 30 | Polybutylene 8910 | Montell | Polybutylene |
| 7 | Polybutylene 0800 | Montell | Polybutylene |
| 11 | Epolene N10 | Eastman | Wax |
| 1 | Irganox 1010 | Ciba Additives | Stabilizer |

EXAMPLE 3

The following adhesive blend was prepared in accordance with the present invention. When tested, the adhesive performed exceptionally well as an elastic attachment adhesive while also providing adequate creep performance after emollient exposure.

| Weight % | Ingredient | Commercial Source | Generic Name |
|---|---|---|---|
| 18 | Eastotac H100 | Eastman | Resin |
| 5 | Escorez 2520 | Exxon | Resin |
| 19 | Polybutylene 8910 | Montell | Polybutylene |
| 19 | Polybutylene 0800 | Montell | Polybutylene |
| 28 | RT2715 | Huntsman | Polyalphaolefin |
| 10 | Epolene N15 | Eastman | Wax |
| 1 | Irganox 1010 | Ciba Additives | Stabilizer |

EXAMPLE 4

Laminations were made between nonwoven topsheet and highloft nonwoven acquisition layer. Adhesive was spiral sprayed at 6 gm/m$^2$ with a 0.5 second open time. The application temperature was 165° C. and the heated air temperature used for spraying was 190° C. Immediately after combining the nonwoven substrates, emollient (petrolatum jelly) was applied to the laminate at 6 gm/m$^2$. The laminations were tested both with and without emollient. The test method was 180° peel strength in the machine-direction at 12 inches/minute. The average peel was reported in grams.

Control: a commercially available construction adhesive containing a styrenic block copolymer and various resins and plasticizers was used. The control adhesive contains no polybutylene and is available from Ato Findley, Inc. under the trade designation H4088.

| Adhesive | Average Peel without emollient (gm) | Average peel with emollient (gm) |
|---|---|---|
| Control | 238 | 47.8 |
| Example 1 | 181 | 188 |

Conclusion: Control sample loses significant bond strength after contact with emollient lotion. This would allow the topsheet to tent, decreasing acquisition of fluids. It could also allow the endseal of the article to open up. It is preferred that the peel strength should be about 100 gm or higher to maintain optimal performance.

EXAMPLE 5

The disposable products made with the current invention would need to be stable while transported, warehoused, and sitting on store shelves. The laminates made in example 4 were subjected to warehouse conditions of 7 days at 49° C. After this elevated temperature storage, the samples were tested again, both with and without emollient.

| Adhesive | Average Peel without emollient (gm) | Average peel with emollient (gm) |
|---|---|---|
| Control | 230 | 11.1 |
| Example 1 | 181 | 231 |

Conclusion: The performance of the control adhesive drops further upon storage. The adhesive of this invention maintains bond strength even after elevated temperature storage conditions. The total loss of strength with the control adhesive would allow separation of the layers and the article to be pulled apart easily. It is preferred that the peel strength should be about 100 gm or higher to maintain optimal performance.

EXAMPLE 6

Laminations were made with three elastic strands (Lycra 740) stretched 300% between two layers of nonwoven. Adhesive was spiral sprayed at 18.6 gm/M$^2$ with a 0.25 second open time. Application temperature was 180° C. for the adhesive and 200° C. for the heated air used for spraying. Immediately after combining the nonwoven substrates, emollient (petrolatum jelly) was applied to the laminate at 6 gm/m$^2$. Laminations with and without emollient were tested for elastic creep performance. Laminations were stretched fully and fastened to a board. The elastic strands were cut, marked, and measured. After aging 4 hours at 100° F., the elastic strands were remeasured and compared to their original length. Creep was calculated as follows: New length divided by original length multiplied by 100=percent retention.

Control: a commercially available elastic attachment adhesive containing a styrenic block copolymer and various resins and plasticizers was used. The control adhesive contains no polybutylene and is available from Ato Findley, Inc. under the trade designation H2494.

| Adhesive | Creep Resistance without emollient (% retention) | Creep Resistance with emollient (% retention) |
|---|---|---|
| Control | 82 | 33 |
| Example 2 | 95 | 84 |
| Example 3 | 97 | 88 |

Conclusion: Under these conditions, acceptable performance would be percent retention greater than 65 percent. The control sample has unacceptable performance when used with an emollient. This is total failure and would allow the elastic strands to be completely loose in the diaper.

EXAMPLE 7

The performance characteristics of a resin in an adhesive are directly related to the compatibility characteristics of the resin in the polymer. A convenient method acceptable to and generally used by those skilled in this art to characterize resin compatibility is by determination of cloud points in suitable solvent systems. From the cloud point values obtained, the resin may be characterized as being aliphatic, aromatic, or a combination of both, polar or non-polar, and having a high or low molecular weight.

For practical purposes, the cloud points may be related to compatibility by measuring MMAP and DACP. MMAP is a measurement of aromatic solubility and determines the aliphatic/aromatic character of the resin. The lower the MMAP value, the more aromatic is the resin. DACP determines the polarity of the resin due to the highly polar nature of the solvent system. Since specific adhesion is related to the polarity of a resin, the DACP cloud point can be used as a specific adhesion indicator. The lower the DACP value, the better is the specific adhesion of a resin. MMAP and DACP data is widely known in the industry and can be obtained from numerous sources, such as Hercules Brochure No. 900-204B entitled "The Hercules Spectrum of Hydrocarbon Resins" dated July, 1995.

Figure 4:
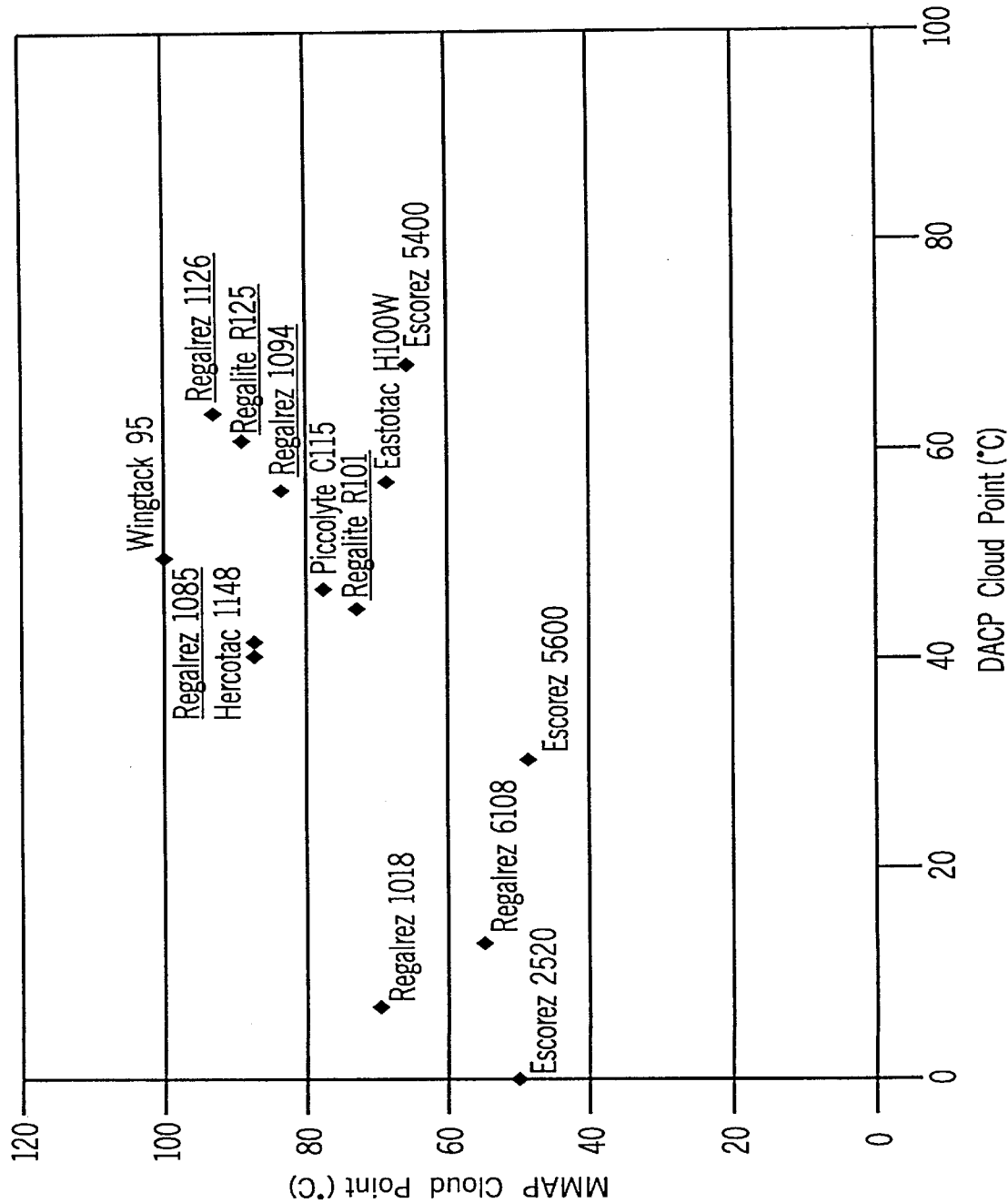
FIG. 4 is a graph illustrating MMAP and DACP cloud point values for various hydrocarbon resins.

When cloud point values are graphically displayed, compatibility application windows may be determined for resin-compatibility with various polymers. FIG. 4 displays the MMAP and DACP cloud point regions to numerous hydrocarbon resins tested by Applicant.

It is generally recognized when formulating that resins with similar mapping on a MMAP/DACP graph have similar compatibility in a given polymer. In this case, however, it is surprisingly not the case. Resins with almost identical mapping have greatly different compatibility, e.g. Regalite R101 and Piccolyte C115, Regalrez 1085 and Hercotac 1148, as will be further demonstrated in Example 8.

EXAMPLE 8

Adhesive thermal stability tests are performed to determine hot melt adhesive viscosity stability and heat aging characteristics. The design of this test is to simulate the excess amount of time or aging that may occur when a hot melt is left for hours at a time in adhesive application equipment. This test will identify the adhesives ability to remain stable by running a viscosity test to compare initial viscosity vs. aged viscosity.

The standard method is to age hot melt in a covered glass jar at 350° F. for 72 hours and stir the sample before removing a small amount for a viscosity measurement. This standard method does not demonstrate the incompatibility issues with these formulations. Even very slight stirring is sufficient to keep the adhesive from separating. The method used herein to test for thermal stability is the same as the standard, except that the adhesive is not disturbed or stirred in any way, and the test is run for longer intervals (up to 7 days). After the aging interval, the samples are observed for signs of incompatibility (opaque color, grainy texture, etc.)

Accordingly, various resins were substituted into Example 2. Thermal stability was measured by holding each adhesive at 350° F. for seven days without any stirring/disturbing of the sample. After 7 days, the sample was observed under bright light. Samples were recorded for cloudiness and grainy texture. The results are reported as follows:

| Resin Trade Designation | Cloud Point MMAP/ DACP | Resin Commercial Source | Resin Type | Cloudiness at 350° F. | Grainy Texture after 7 days at 350° F. undisturbed |
|---|---|---|---|---|---|
| Regalrez 1085 | 85/40 | Hercules | Fully hydrogenated styrene, vinyl toluene | Completely clear | None |
| Regalrez 1094 | 83/54 | Hercules | Fully hydrogenated styrene, alpha methyl styrene | Completely clear | None |
| Regalrez 1126 | 91/62 | Hercules | Fully hydrogenated styrene, alpha methyl styrene | Completely clear | None |
| Arkon P100 | 76/45 | Arakawa | Fully hydrogenated C9 | Completely clear | None |
| Regalite R101 | 78/46 | Hercules | Fully hydrogenated C9 | Completely clear | None |
| Wingtack 95 | 95/49 | | C5 (non-hydrogenated) | Slight haze | None |
| Regalrez 6108 | 54/15 | Hercules | Partially hydrogenated styrene, alpha methyl styrene | Opaque | Grainy |
| Hercotac 1148 | 85/39 | Hercules | C5/C9 | Opaque | Grainy |
| Piccolyte C115 | 79/45 | Arizona | Terpene | Opaque | Grainy |
| Eastotac H100W | 59/72 | Eastman | Fully hydrogenated mixed feed | Opaque | Grainy |
| Escorez 5400 | 70/71 | Exxon | Fully hydrogenated DCPD | Opaque | Grainy |

Also, after the aging interval is complete, the adhesive was poured from the jar onto a release surface. Samples from the top and bottom of the jar were tested for viscosity. The top and bottom viscosity measurements should be equal (within the error of the measurement) if the resin is compatible with the polymer. Below are some measurements taken:

| | Viscosity (cP) at 325° F. | |
|---|---|---|
| | Top of Jar | Bottom of Jar |
| Standard SIS adhesive | 950 | 840 |
| Regalite R101 | 5650 | 5450 |
| Eastotac H100W | 8450 | 3390 |
| Escorez 5400 | 6040 | 3090 |

As illustrated, the SIS and Regalite R101 adhesives have relatively consistent top and bottom viscosities, while the Eastotac H100W and Escorez 5400 have a much higher viscosity at the top compared to the bottom, indicating their incompatibility with polybutylene.

Conclusions:

The choice of resin is critical. Preferably the resin should be a fully hydrogenated C9 resin. Hydrogenation is a technique that is used to increase the stability of a resin. It also changes the compatibility of the resultant resin. For use in the present invention, it is important that the resin be essentially fully hydrogenated.

Regalrez 1094, 1126 and 6108 are all copolymers of alpha methyl styrene and styrene. Regalrez 1094 and 1126 are both essentially 100 percent hydrogenated, as indicated by the "1" in the grade designation. The last three digits indicate the softening point of the resin. Regalrez 1094 is therefore 100 percent hydrogenated with a softening point of 94° C. Regalrez 1126 is 100 percent hydrogenated with a softening point of 126° C., and Regalrez 6108 is 60 percent hydrogenated with a softening point of 108° C.

For example, in the above table, Regalrez 6108 is chemically identical to Regalrez 1094 and 1126, with the exception that Regalrez 6108 is only 60 percent hydrogenated and the other two are essentially 100 percent hydrogenated. All of these resins are available from Hercules, Inc. It is clear from the table that Regalrez 6108 is not compatible in the system while the other two are very compatible. In a similar manner, Arkon P100, which is fully hydrogenated is very compatible in the system. Arkon F100 and SM10, which are the same C9 type feed, but not fully hydrogenated are not compatible and produce opaque adhesives.

The other critical selection criterion is that the resin be a "C9" type. The C9 feed is a highly aromatic feed used as a base to manufacture tackifying resins and can be derived from one of two sources. It can be a "pure monomer" type or can be obtained from a cracked naphtha feedstream. A pure monomer feed is one in which the feedstream has been distilled or otherwise refined to yield a relatively pure stream of a given monomer. For example, the feed can be largely alpha-methyl styrene, vinyl toluene, styrene, etc. This pure monomer feedstream can then be polymerized either neat or in various combinations to yield a resinous intermediate which is then hydrogenated to give the finished resin. Examples of these resins include the Regalrez materials described earlier which can be obtained from Hercules, Inc.

Another way in which these feeds can be obtained is from the process of steam cracking of naphtha. This process is widely used in the production of gasoline. During the distillation process of naphtha, a C9 aromatic olefin stream can be obtained. This feedstream is composed of various components, including styrene, alpha-methyl styrene, vinyl toluene, indene, methyl indene, dicyclopentadiene, etc. Although some smaller amount of monomers are typically present which are higher (C 10) or lower (C8) than C9, this feedstream is routinely called a C9 feed. This C9 feedstream is polymerized and hydrogenated in a manner similar to that used for the pure monomer resins above. To be useful in this invention the C9 content should be relatively high. Examples of these types of resins are the Arkon P resins, available from Arakawa Chemical Inc. and Regalite R101 available from Hercules, Inc.

Wingtack 95 is not hydrogenated and therefore starts off darker in color (Gardner 4 versus Water-white) and is not as thermally stable as a hydrogenated pure monomer or C9 hydrocarbon resin.

Thus, for optimum compatibility, resins should be fully hydrogenated. Most preferably, the fully hydrogenated resins should be of the pure monomer (alpha methyl styrene, styrene, vinyl toluene, etc.) type or of the highly pure C9 type.

What is claimed is:

1. A laminate structure for use in a disposable absorbent article, comprising:
    a substrate;
    a topsheet having a first surface facing said substrate and a second skin-engaging surface;
    an emollient in contact with the second skin-engaging surface of said topsheet; and
    an emollient resistant hot melt adhesive disposed between and bonding said substrate to said topsheet, said adhesive consisting essentially of a blend of:
    (a) about 10% to about 65% by weight of a polybutylene copolymer, homopolymer, or blend thereof;
    about 15% to about 70% by weight of a tackifying resin, said tackifying resin is selected from the group consisting of fully hydrogenated aromatic hydrocarbon resins, fully hydrogenated aliphatic hydrocarbon resins, and mixtures thereof;
    about 0% to about 30% by weight of a plasticizer;
    about 0% to about 20% by weight of a wax; and
    about 0.1% to about 2% by weight of a stabilizer, wherein the minimum polymer content is 20% by weight.

2. The laminate structure of claim 1 wherein the plasticizer is selected from the group consisting of mineral oil and polybutene.

3. The laminate structure of claim 1 wherein the adhesive comprises:
    (a) about 37% by weight of a polybutylene copolymer and homopolymer blend;
    (b) about 51% by weight of a tackifying resin;
    (c) about 11% by weight of a wax; and
    (d) about 1% by weight of a stabilizer.

4. The laminate structure of claim 1 wherein said substrate is composed of a material selected from the group consisting of absorbent cellulosic material, polyolefins, superabsorbent polymers, polyesters, elastics and combinations thereof.

5. The laminate structure of claim 1 wherein said topsheet is selected from the group consisting of nonwoven fabric, tissue, absorbent fluff, superabsorbents, elastics, a polyolefin, and combinations thereof.

6. The laminate structure of claim 5 wherein said polyolefin comprises a polyethylene or polypropylene layer.

7. The laminate structure of claim 1 wherein the disposable absorbent article is a diaper.

8. The laminate structure of claim 1 wherein the disposable absorbent article is a feminine care pad.

9. The laminate structure of claim 1 wherein said resin is a fully hydrogenated C9 type.

10. The laminate structure of claim 1 wherein said emollient is coated on said topsheet.

* * * * *